US00PP36905P2

(12) United States Plant Patent
Zlesak

(10) Patent No.: US PP36,905 P2
(45) Date of Patent: Sep. 2, 2025

(54) SHRUB ROSE PLANT NAMED 'ZLELisaAnnHansen'

(50) Latin Name: *Rosa hybrida*
Varietal Denomination: ZLELisaAnnHansen

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 0 days.

(21) Appl. No.: 18/831,370

(22) Filed: Dec. 17, 2024

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 5/0222
See application file for complete search history.

*Primary Examiner* — Kent L Bell

(57) ABSTRACT

'ZLELisaAnnHansen' is a new and distinct cultivar of *Rosa hybrida* having a mounded, well-branched, very compact plant habit; vigorous growth; double flowers typically borne in clusters of 8 or more; flowers with relatively long and straight peduncles that elevate and separate individual flowers; medium to light pink petal color; continuous flowering throughout the growing season; resistance to major fungal diseases impacting roses; and ability to root and grow vigorously from softwood and semi-hardwood stem cuttings.

7 Drawing Sheets

Latin name of the plant claimed: *Rosa hybrida.*
Varietal denomination: 'ZLELisaAnnHansen'.

BACKGROUND OF THE INVENTION

This invention relates to a new and distinct variety of compact shrub rose. The varietal denomination of the new variety is 'ZLELisaAnnHansen'. The pollination that led to 'ZLELisaAnnHansen' occurred in River Falls, Wisc. in 2018 and the population from which 'ZLELisaAnnHansen' was selected as a superior and distinct genotype germinated in spring 2019. The population, from which 'ZLELisaAnnHansen' was selected, was planted in a ground bed in River Falls, Wisc. in summer 2019, and 'ZLELisaAnnHansen' was selected as an exceptional unique genotype and first asexually propagated in River Falls, Wisc. summer 2020. In all clonally-propagated generations to date, the unique and characteristic growth and flowering traits of 'ZLELisaAnnHansen' have been stable.

BRIEF SUMMARY OF THE INVENTION

The objective of my breeding program is to develop healthy and winter hardy roses to USDA cold hardiness zone 4 with attractive ornamental features. These goals were substantially achieved in 'ZLELisaAnnHansen', as evidenced by the following unique combination of characteristics that are outstanding in the new variety and that distinguish it from its maternal parent, as well as from all other varieties of which I am aware:

1. Mounded, well-branched, very compact plant habit;
2. Vigorous growth;
3. Double flowers typically borne in clusters of 8 or more;
4. Flowers with relatively long and straight peduncles that elevate and separate individual flowers;
5. Medium to light pink petal color;
6. Continuous flowering throughout the growing season;

7. Resistance to major fungal diseases impacting roses;
8. Ability to root and grow vigorously from softwood and semi-hardwood stem cuttings.

Asexual reproduction of this new variety by rooting softwood and semi-hardwood cuttings, as performed at River Falls, Wisc., shows that the foregoing and all other characteristics and distinctions come true to form and are established and transmitted through succeeding propagations.

Comparison with Parent

Both 'ZLELisaAnnHansen' and its maternal parent, 7BA3 (unreleased and unpatented seedling selection) have similar flower color, petal number, and flower form. They differ in that 7BA3 is a larger growing plant that has weaker stems that tend to lodge, a more elongated and conical shaped inflorescence, larger flowers and leaves, typically more leaflets per leaf, a lighter green leaf color, and produces anthers. Anthers have not been observed in flowers of 'ZLELisaAnnHansen'. 'ZLELisaAnnHansen' has a much more dense and symmetrical plant habit relative to 7BA3. 'ZLELisaAnnHansen' was raised from open-pollinated seed collected from 7BA3. The paternal parent of 'ZLELisaAnnHansen' is unknown. Both 'ZLELisaAnnHansen' and 7BA3 have been reliably winter hardy in USDA cold hardiness zone 4 and display resistance to the typical fungal diseases of roses.

Comparison with Similar Variety

A rose variety with similarity to 'ZLELisaAnnHansen' is 'ZLEMarianneYoshida' (marketed under the names Oso Easy® Petit Pink, Oso Happy® Petit Pink, and Petite PinkTM; U.S. Plant Pat. No. 22,205), a compact rose of the shrub commercial class. Both 'ZLELisaAnnHansen' and 'ZLEMarianne Yoshida' have double blooms borne in clusters, comparable mature plant size, and are resistant to common fungal diseases that infect roses. The key difference is that 'ZLELisaAnnHansen' has a more dense and symmetrical growth habit with smaller flowers, stems, and leaves. The flowers of 'ZLELisaAnnHansen' are more numerous and open and mature to a lighter shade of pink than 'ZLEMarianne Yoshida'.

BRIEF DESCRIPTION OF THE DRAWINGS

The accompanying illustrations show typical specimens of the vegetative growth and flowers of 'ZLELisaAnnHansen' in different stages of development, depicted in color as nearly true as it is reasonably possible to make the same in color illustrations of this character.

DETAILED BOTANICAL DESCRIPTION

Figure 1:
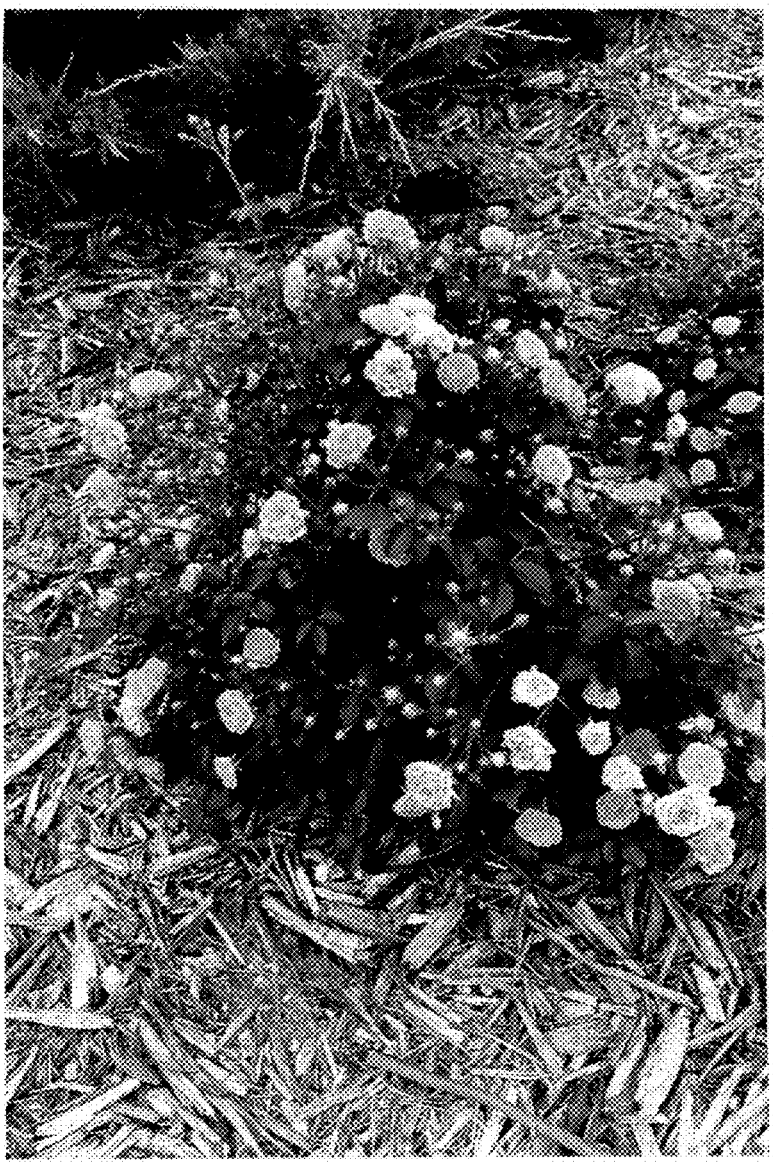
FIG. 1 illustrates a one-year-old plant in a garden bed.
Figure 2:
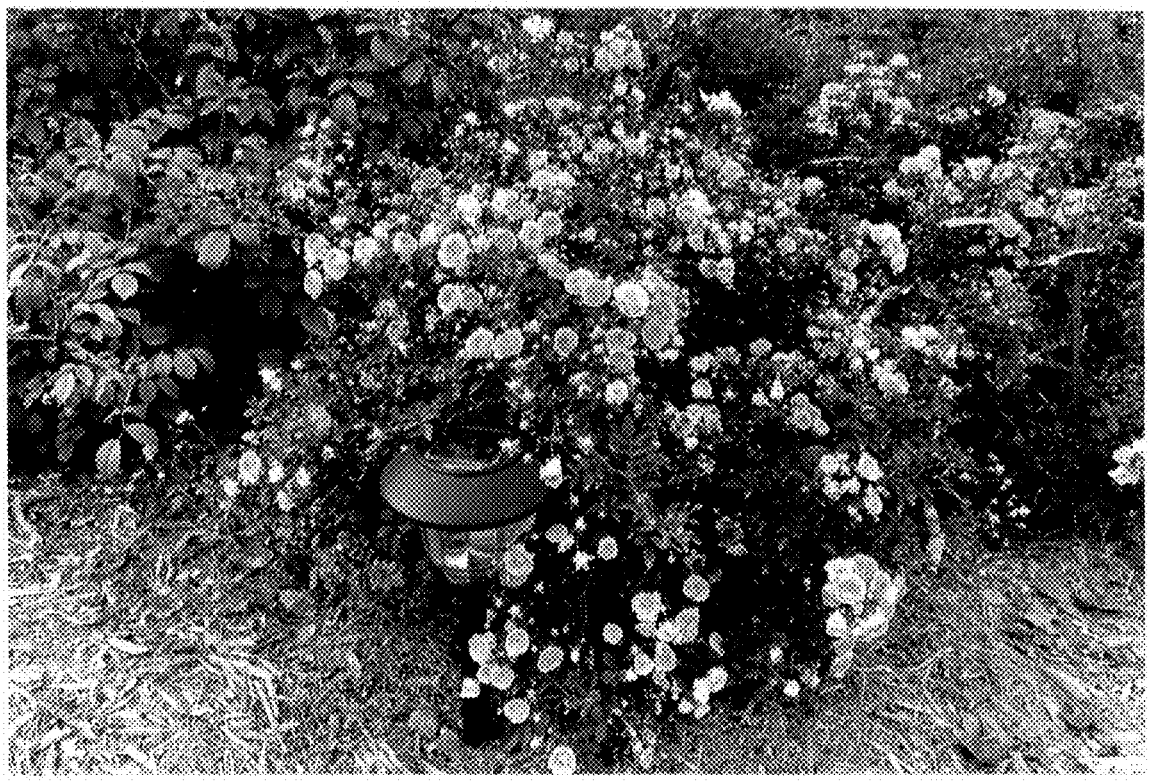
FIG. 2 illustrates the original ortet in a garden bed during its sixth growing season.
Figure 3:
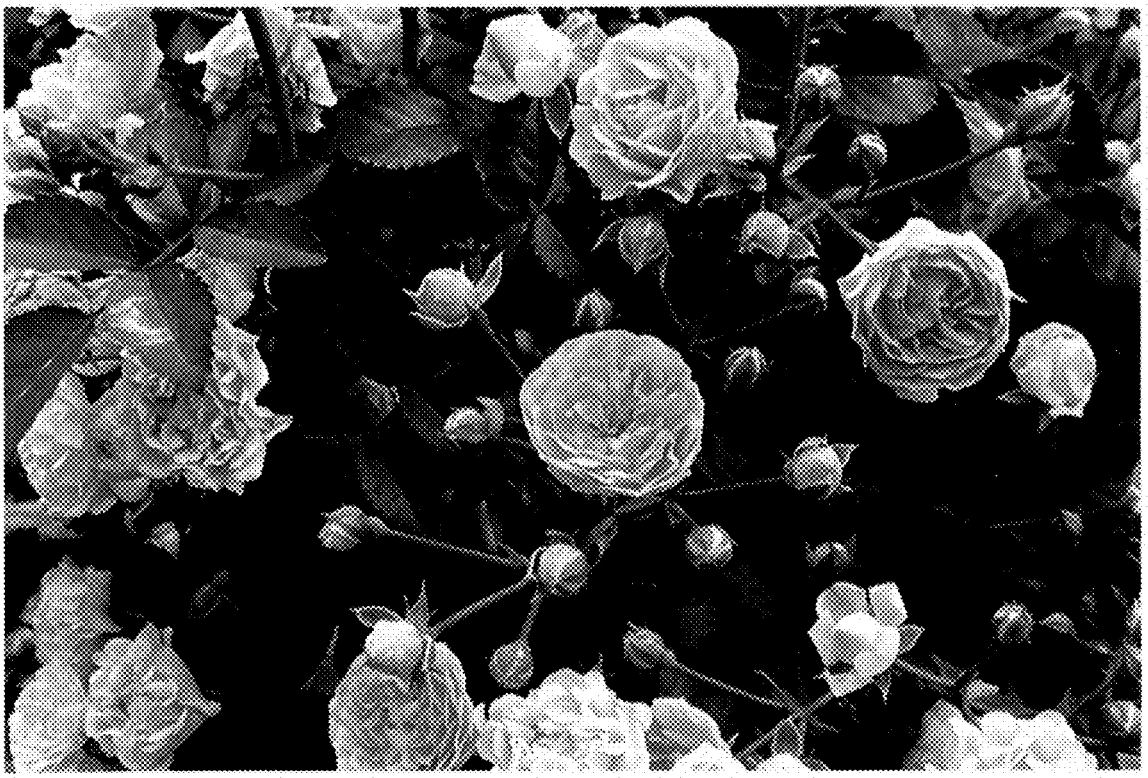
FIG. 3 illustrates flowers in a range of development from tight buds to fully open flowers.
Figure 4:
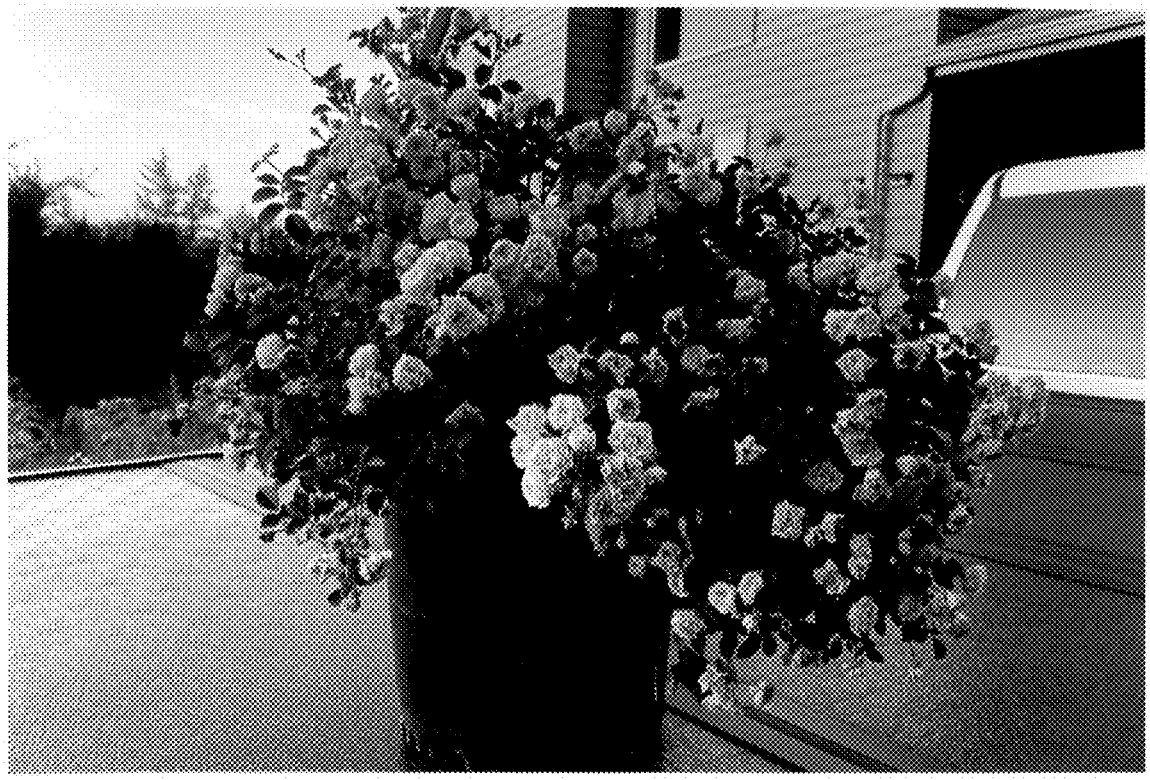
FIG. 4 illustrates a two-year-old plant growing in a container.
Figure 5:
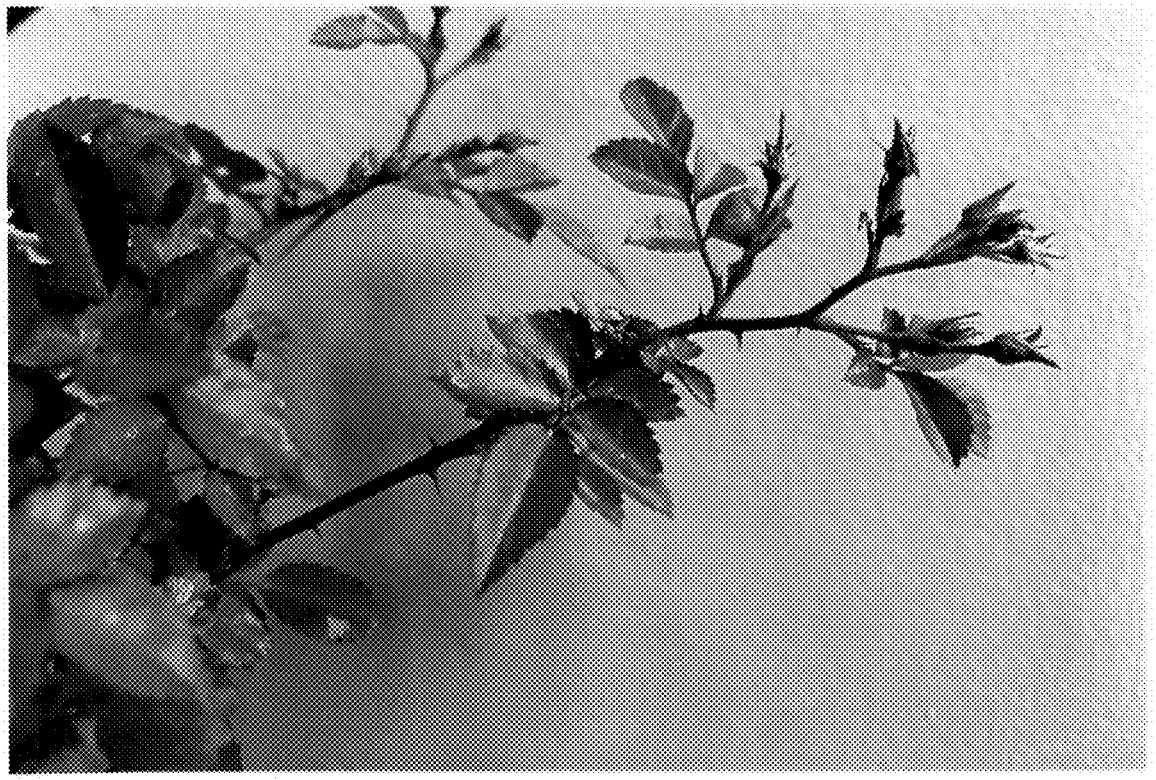
FIG. 5 illustrates prickles and leaves on young stems.
Figure 6:
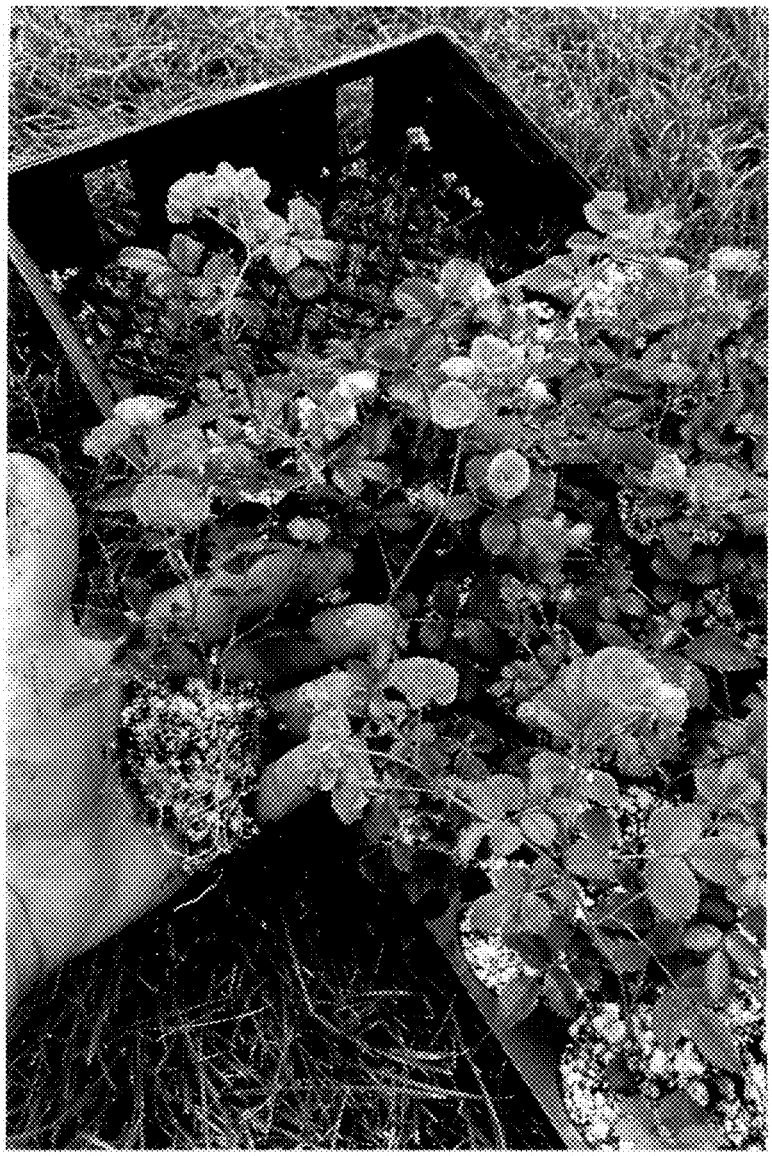
FIG. 6 illustrates rooted cuttings ready for transplant four weeks after sticking.
Figure 7:
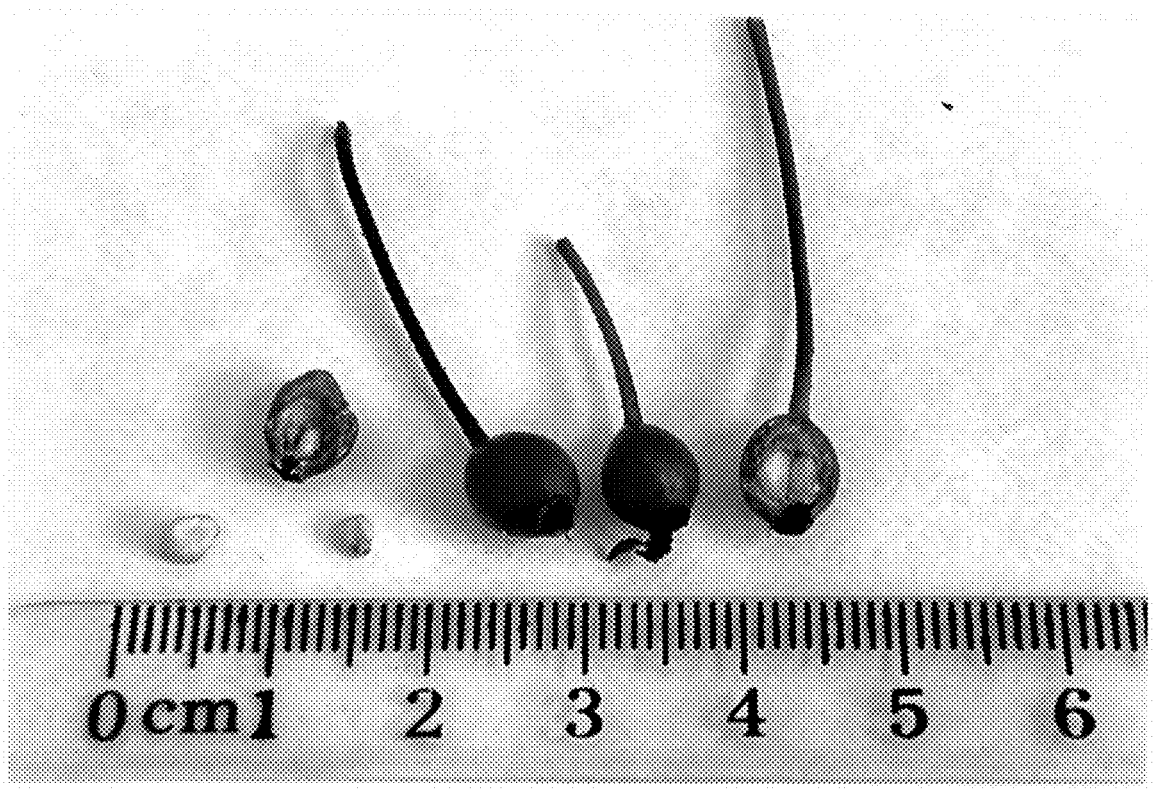
FIG. 7 illustrates mature hips and achenes.

The following is a detailed description of my new rose cultivar with color descriptions using terminology in accordance with the sixth edition of The Royal Horticultural Society (London) Colour Chart (2015), except where ordinary dictionary significance of color is indicated. The phenotype of the new cultivar may vary with differences in environmental, climatic, and cultural conditions, as it has not been tested under all possible environmental conditions. Descriptions are based on observations of the original ortet during its sixth growing season planted in a garden bed in River Falls, Wisc.

Parentage:

*Originating parents*.—The maternal parent of 'ZLELisaAnnHansen' is 7BA3 (unpatented), a proprietary seedling in my breeding program. The seed that led to 'ZLELisaAnnHansen' was from an open-pollination event and the paternal parent is unknown.

Classification:

*Botanical*.—*Rosa hybrida*.

*Commercial*.—Shrub rose.

Flower:

*Blooming Habit*.—Continuous.

Bud:

*Size*.—9-12 mm long and 4-6 mm in diameter when the petals start to unfurl.

*Form*.—The bud form is ovoid and pointed.

*Color*.—When sepals first divide, visible petal color is Red-Purple Group 62D. When half blown, the upper or adaxial sides of the petals are closest to Red-Purple Group 67D on the distal end (approximately 85% of the petal surface) and White Group N155D at the proximal end (approximately 15% of the petal surface). The lower or abaxial sides of the petals have a background color of Red-Purple Group 63C. The base or proximal end of the petals (<2 mm) are White Group N155D.

*Sepals*.—Color: Green Group 137D on the abaxial side and Green Group 138B on the adaxial side. Length: 8-10 mm. Width: 3 mm. Shape: ovate to oblong with acuminate tips. Surface texture: Adaxial, Hoary. Abaxial, Generally smooth with some very small glandular hairs (<0.2 mm). There are three lightly appendaged sepals. There are two unappendaged sepals which have hoary edges.

*Receptacle*.—Color: Yellow-Green Group 144A. Shape: round to slightly elliptic. Size: Small, about 2.5-3.0 mm wide and 4 mm long. Surface: glabrous.

*Peduncle*.—Length: Averaging about 15-20 mm. Width: 1 m. Surface: primarily glabrous with very small glandular hairs (<0.2 mm). Color: Yellow-Green Group 144A. Strength: Stiff and straight.

Bloom:

*Size*.—Small. Typical open diameter is 20 -24 mm; typical height approximately 1.2 cm.

*Borne*.—Typically in clusters of 8 to 35 blooms per stem; the mature ortet in peak bloom has approximately 400 open blooms at once.

*Stems*.—Strength: Strong. Length: Typically about 8-13 cm for side stems in the canopy and up to 35 cm for vigorous stems coming from the base of the plant. Stem diameter: Varies and is typically 2-5 mm. Larger stems arising from the base of the plant are about 4-5 mm in diameter, while smaller stems that are typically secondary or tertiary stems arising within the plant canopy are typically 2-3 mm in diameter. Internode length:2.0-4.0 cm.

*Form*.—When blooms first open: Cupped with petals unfurling in a symmetrical manner that is commonly called a decorative form by rose growers and exhibitors. When blooms fully open: Slightly cupped to flat.

*Permanence*.—Blooms retain their form to the end.

*Petalage*.—Double blooms with petals and petaloids typically totaling 50-60.

*Color*.—The adaxial side of petals are closest to Red-Purple Group 67D and this color covers about 85% of the petal surface at the distal end with the proximal end being White Group N155D (about 15%). The abaxial side of the petals are Red-Purple Group 63C over most of the petal with only about ≤2 mm of the proximal end being White Group N155D.

*Discoloration*.—The general tonality of the adaxial petal surface of a fully open bloom at the first day through the third day: Red-Purple Group 67D. By day 8 the general tonality of the adaxial petal surface is White Group N155C. The general tonality of the abaxial petal surface of a fully open bloom at the first day through the third day: Red-Purple Group 63C. By day eight the abaxial petal surface has a general tonality closest to White Group N155D.

*Fragrance*.—Slight. Character of fragrance: Sweet.

Petals and Petaloids:

*Texture*.—Thick and satiny to the touch.

*Length*.—0.8-1.2 cm.

*Width*.—The outermost petals of the bloom tend to be wider and are typically 0.7-1.0 cm and the innermost petaloids are more narrow and are typically 0.4 cm.

*Shape*.—The outermost petals are obcordate and the shape of the petaloids transitions moving towards the center of the flower to obovate and then finally oblong. About 5-10 of the innermost petals are often folded in half with adaxial sides together and specifically folded so the distal end of the petal located adjacent to the proximal end.

*Margin*.—Entire.

*Apex shape*.—Obcordate for the outermost petals and rounded for the petals towards the center of the bloom.

*Base shape*.—Acute for the outermost petals and transitioning to cuneate for the inner petaloids.

*Form*.—Flat to slightly cupped.

*Arrangement*.—Multiple rows of overlapping petals.

*Petaloids*.—Roses have five true petals (except for *Rosa sericea* which typically has four) and all additional petal-like appendages are botanically petaloids. Petaloids are botanically stamens, or in some cases also pistils, that develop into petal-like structures. However, petaloids that do not have obvious remnant stamen development are often called petals in common vernacular in United States Plant Patents and the popular press. 'ZLELisaAnnHansen', like typical roses, has five true petals and typically between 45-55 petaloids that look like typical petals. Pistils of 'ZLELisaAnnHansen' appear to have normal morphology and have not been observed to develop into petaloids. The color of the petal-like petaloids is comparable to the color of the five true petals and the size and shape distinctions between petals and petaloids are described above.

*Persistence*.—Petals and petaloids typically drop off cleanly before drying.

*Lastingness*.—On the plant: Long (about 10 days). As a cut flower: Moderate (about 7 days).

Reproductive Parts:

*Stamens*.—None observed. Dissected flowers did not have stamens.

*Pistils*.—Number per flower: 15-20. Styles — Color: Yellow-green Group 145C. Length: 4-6 mm. Width: 0.2 mm. Stigmas — Color: Yellow-Green Group 153D. Length: 0.5 mm. Width: 0.5 mm. Ovary — Color of immature ovary: White Group 155C. Length: 0.75 mm. Width: 0.25 mm.

*Hips*.—The fleshy portion of rose hips is hypanthium tissue and inside that tissue are achenes-single-seeded fruits with a hard pericarp surrounding the embryo. Hips are very rarely seen on 'ZLELisaAnnHansen' (<0.5% of blooms typically result in hips), even with abundant pollinators and a rich diversity of male-fertile rose genotypes growing nearby. For hips that are present, sepals typically fall off before ripening. Hypanthium: Color immature: Yellow-Green Group 144A. Color mature: Greyed-Orange Group N172A. Shape: Generally oval. Size: 8-9 mm long and 6-8 mm wide.

*Achenes* (*ripe*).—Color: Yellow Green Group 150D. Shape: Irregular since they press up against each other and the hypanthium wall tightly. Size: 3-4 mm in length and width. Typically there are 1-3 achenes per hip.

Plant:

*Form*.—Mounded and slightly spreading.

*Growth*.—Very vigorous, well-branched, and dense.

*Age at mature size*.—Typically 3 years.

*Mature plant*.—Height is 60 cm and width is 85 cm.

Leaf:

*Type*.—Leaves are pinnately compound with typically five or seven leaflets.

*Arrangement*.—Leaves are alternately arranged on stems.

*Overall Leaf Size*.—Small (4.0-6.0 cm long and 3.0-4.5 cm wide).

*Quantity*.—Normal.

*Leaflet color*.—New foliage: Adaxial side: Yellow-Green Group 146B and where full sun hits the new foliage there is a light overlay of Red-Purple Group 60B. Abaxial side: Yellow Green Group 146B. Old foliage: Adaxial side: Green Group 139A. Abaxial side: Green Group 138A.

*Leaflet venation pattern*.—Pinnate reticulate.

*Leaflet venation color*.—The color of the veins is the same as that of the overall leaf blade. New foliage: Adaxial side: Yellow-Green Group 146B and where full sun hits the new foliage there is a light overlay of Red-Purple Group 60B that is about 1 mm around the margin. Abaxial side: Green Group 138B. Old foliage: Adaxial side: Green Group 137A. Abaxial side: Green Group 138A.

*Leaflet size*.—Terminal leaflets: Small (1.8-2.2 cm long and 1.4-1.6 cm wide). Non-terminal leaflets: Small (1.5-1.8 cm long and 1.2-1.5 cm wide).

*Leaflet shape*.—Elliptic to ovate.

*Leaflet base shape*.—Rounded.

*Leaflet apex shape*.—Acute to slightly acuminate.

*Leaflet texture*.—Semi-glossy to glossy, rugose. On the adaxial side of leaflets the veins are very slightly recessed and on the abaxial side they are slightly elevated relative to the general leaflet blade.

*Leaflet edge*.—Serrated with small single serrations (about 1 mm long).

*Petiole*.—Color — Yellow-Green Group 144A.

*Petiole*.—1.75-2.25 cm in length and 1 mm in width.

*Petiole rachis*.—Color: Green Group 144A.

*Petiole rachis*.—2.0-3.0 cm in length and 1 mm in width.

*Petiole rachis*.—Texture — Generally smooth with small periodic prickles 0.5 mm in length and 0.1 mm in width).

*Petiole*.—Generally smooth with small prickles (1.0-1.5 mm in length and <0.3 mm in width). Prickles typically are Greyed-Red Group 181D in color.

*Fall foliage color*.—Color: Yellow-Orange Group 15A on the adaxial side of the leaflets and between Yellow Group 13A and 13B for abaxial side of the leaflets and for both sides of the rachis and stipules.

*Stipules*.—Short (about 0.6-0.7 cm in length and 0.2 cm in width). Color: Yellow-Green Group 144A, edges with several relatively parallel and very narrow appendages (0.5-1.0 mm long and 0.2 mm wide).

*Disease resistance*.—Resistant to powdery mildew (*Podosphaera pannosa*), black spot (*Diplocarpon rosae*), and rust (*Phragmidium tuberculatum*) under normal growing conditions.

*Pest resistence*.—Not observed.

Wood:

*New wood*.—Color: Generally Yellow-Green Group 146B. Bark: Smooth.

*Old wood*.—Color: Yellow-Green Group 144B. Bark: Smooth.

Typical stem prickles:

*Quantity*.—Relatively few to typical with up to 3 per internode.

*Form*.—Straight to slightly downward hooked.

*Length*.—3-5 mm.

*Width*.—1-2 mm near stem and narrowing to tip.

*Color when young*.—Greyed-Red Group 181D. If in full sun, there can be an overlay of Red-Purple Group 60B.

*Color when mature*.—Orange-White Group 159A.

Small, secondary stem prickles:

*Quantity*.—None.

Cytology:

*Ploidy*.—Diploid (2n=2x=14). Meristematic root tip cells in the stages of prophase and metaphase of mitosis were observed to have 14 chromosomes under a light microscope at 400x magnification.

Winter Hardiness: Consistently crown hardy with typically some above ground stem survival in United States Department of Agriculture cold hardiness zone 4.

I claim:

1. A new and distinct variety of rose plant of the shrub commercial class named 'ZLELisaAnnHansen', substantially as herein shown and described, characterized particularly by its mounded, well-branched, very compact plant habit; vigorous growth; double flowers typically borne in clusters of 8 or more; flowers with relatively long and straight peduncles that elevate and separate individual flowers; medium to light pink petal color; continuous flowering throughout the growing season; resistance to major fungal diseases impacting roses; and ability to root and grow vigorously from softwood and semi-hardwood stem cuttings.

* * * * *